(12) United States Patent
Chen et al.

(10) Patent No.: US 11,485,756 B2
(45) Date of Patent: Nov. 1, 2022

(54) CYCLIC RGD PEPTIDE AND METHOD FOR PREPARING THE SAME

(71) Applicant: NATIONAL TSING HUA UNIVERSITY, Hsinchu (TW)

(72) Inventors: Chien-Tien Chen, Hsinchu (TW); Shiue-Shien Weng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 179 days.

(21) Appl. No.: 16/860,687

(22) Filed: Apr. 28, 2020

(65) Prior Publication Data

US 2021/0230222 A1    Jul. 29, 2021

(30) Foreign Application Priority Data

Jan. 16, 2020 (TW) .................. 109101475

(51) Int. Cl.
 *C07K 5/12* (2006.01)
 *C07K 7/64* (2006.01)

(52) U.S. Cl.
 CPC ............... *C07K 5/123* (2013.01); *C07K 5/12* (2013.01); *C07K 7/64* (2013.01)

(58) Field of Classification Search
 None
 See application file for complete search history.

(56) References Cited

U.S. PATENT DOCUMENTS

2018/0298060 A1* 10/2018 Chen .................... C07K 7/64

FOREIGN PATENT DOCUMENTS

| TW | 201839008 A | 11/2018 |
|---|---|---|
| WO | 2009124754 A | 10/2009 |

* cited by examiner

*Primary Examiner* — Kevin S Orwig
(74) *Attorney, Agent, or Firm* — Muncy, Geissler, Olds & Lowe, P.C.

(57) ABSTRACT

A method for preparing a cyclopeptide and a cyclopeptide preparing by the method are disclosed. The method includes the following steps: (A) providing compounds represented by the following formulas (I-1) and (I-2):

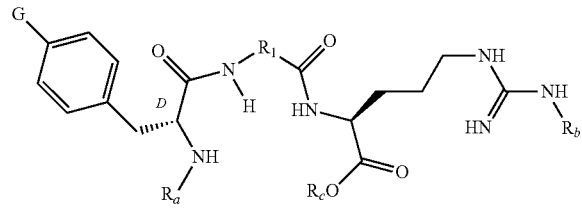

wherein, G, $R_a$, $R_b$, $R_c$, $R_d$, and $R_e$ are defined in the specification; (B) performing a reaction between the compounds of formulas (I-1) and (I-2) to obtain a compound represented by the following formula (I-3):

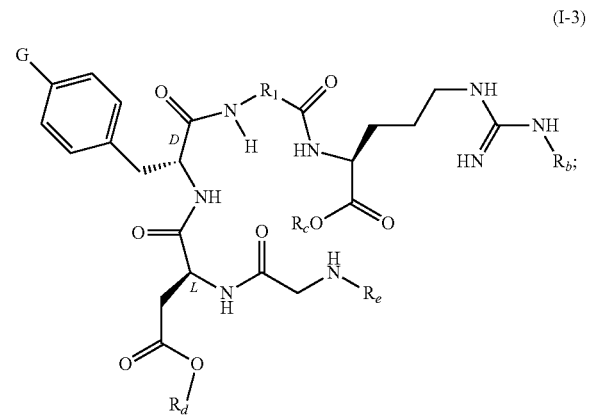

and (C) performing a cyclization reaction of the compound of formula (I-3) with a catalyst of formula (II) and deprotection to obtain a compound represented by the following formula (III):

(Continued)

-continued $$M(O)_m L^1_y L^2_z \quad (II)$$

wherein, G', Q, M, L$^1$, L$^2$, m, y, and z are defined in the specification.

12 Claims, 1 Drawing Sheet

CYCLIC RGD PEPTIDE AND METHOD FOR PREPARING THE SAME

CROSS REFERENCE TO RELATED APPLICATION

This application claims the benefits of the Taiwan Patent Application Serial Number 109101475, filed on Jan. 16, 2020, the subject matter of which is incorporated herein by reference.

BACKGROUND OF THE INVENTION

1. Field of the Invention

The present disclosure relates to a cyclopeptide and method for preparing the same. More specifically, the present disclosure relates to a method for preparing a cyclopeptide by catalyst.

2. Description of Related Art

Peptides have found widespread uses in various fields, for example, topical or cosmetic skin care uses. Among the known peptides, the peptide with arginine (R)-glycine (G)-aspartate (D) motif is found as a common unit in cellular recognition.

It is known that the peptide containing RGD motif can bind to the intergrin RGD binding site, and can be used to coat synthetic scaffolds in tissue engineering to enhance cellular attachment by mimicking in vivo conditions.

In the conventional method for preparing the peptide containing RGD motif, coupling agents have to be used to catalyze the peptide synthesis, and a large amount (such as 1 to 5 equivalents) of the coupling agents are needed for the reaction. However, the cost of the coupling agents is high, leading to the high production cost of the peptide, and not all peptides obtained can be used unless with extensive purification to remove the contaminants and/or side products from the coupling reagents.

Therefore, it is desirable to provide a novel method for preparing the cyclopeptide containing RGD motif to be widely applied to various fields.

SUMMARY OF THE INVENTION

In view of this, the present disclosure provides a cyclopeptide and novel catalytic method for preparing the same. In the method, the synthesis of the cyclopeptide is catalyzed by a catalyst to reduce production cost and improve product purity. In addition, the prepared cyclopeptide is allows for favorable long term storage.

The present disclosure provides a method of preparing a cyclopeptide, comprising the following steps (A) to (C).

Step (A) is to provide compounds represented by the following formulas (I-1) and dipeptide (I-2) from commercial source or by the preparation method of the present disclosure, (I-1)

(I-2)

wherein, $R_a$, $R_b$ and $R_e$ are each independently a protection group;

$R_c$ and $R_d$ are each independently alkyl, cycloalkyl, aryl or heteroaryl;

G is H or O-t-Bu; and

$R_1$ is in which $R_2$ and $R_3$ are each independently H or $C_{1-6}$ alkyl; X is O, S, $CH_2$, or N—$R_4$, in which $R_4$ is H, $C_{1-6}$ alkyl, $(CH_2CH_2O)_nH$, —C(=O)—$C_{1-15}$ alkyl, —C(=O)$CH_2$$(OC_2H_4)_n$OR' or C(=O)$(C_2H_4)_2$C(=O)O$(C_2H_4O)_n$R', in which n=1-3 and R' is H or $CH_3$;

Step (B) is to perform a reaction between the compounds of formulas (I-1) and (I-2) to obtain a compound represented by the following formula (I-3):

(I-3)

Step (C) is to perform a cyclization reaction of the compound of formula (I-3) with a catalyst of formula (II) and deprotection to obtain a compound represented by the following formula (III), (III)

$M(O)_m L^1{}_y L^2{}_z$ (II)

wherein G' is H or OH;
Q is halogen, OC(O)CF₃, or OC(O)CH₃;
M is a metal selected from the group consisting of IVB, VB, VIB and actinide groups;
$L^1$ and $L^2$ respectively is a ligand;
m and y are integers greater than or equal to 1; and
z is an integer greater than or equal to 0.

The present disclosure also provides another method for preparing a cyclopeptide, comprising the following steps (a) to (d).

Step (a) is to provide compounds represented by the following formulas (I-1) and N- and O-protected aspartic acid (I-4) by commercial source or the preparation method of the present disclosure, (I-1)

(I-4)

wherein, $R_a$, $R_b$ and $R_e$ are each independently a protection group;
$R_c$ and $R_d$ are each independently alkyl, cycloalkyl, aryl or heteroaryl;
G is H, or O-t-Bu; and
$R_1$ is

[structure with X, R₂, R₃]

in which $R_2$ and $R_3$ are each independently H or $C_{1-6}$ alkyl; X is O, S, CH₂, or N—R₄, in which $R_4$ is H, $C_{1-6}$ alkyl, $(CH_2CH_2O)_nH$, —C(=O)—$C_{1-15}$ alkyl, —C(=O)CH₂$(OC_2H_4)_n OR'$ or $C(=O)(C_2H_4)_2C(=O)O(C_2H_4)_n R'$, in which n=1-3, R' is H or CH₃.

Step (b) is to perform a reaction between the compounds of formulas (I-1) and (I-4) to obtain a compound represented by the following formula (I-5):

(I-5)

Step (c) is to perform a reaction between the compound of formula (I-5) and the compound represented by the following formula (I-6) to obtain a compound represented by the following formula (I-7):

(I-6)

(I-7)

wherein $R_f$ is alkyl, cycloalkyl, aryl, or heteroaryl.

Step (d) is to perform a cyclization reaction of the compound of formula (I-7) with the catalyst of formula (II) and deprotection to obtain a compound represented by the following formula (III):

(III)

(II)

wherein G' is H or OH;

Q is halogen, OC(O)CF$_3$, or OC(O)CH$_3$;

M is a metal selected from the group consisting of IVB, VB, VIB and actinide groups;

L$^1$ and L$^2$ respectively is a ligand;

m and y are integers greater than or equal to 1; and z is an integer greater than or equal to 0.

In the present disclosure, R$_a$ and R$_e$ may be fluorenylmethyloxycarbonyl (Fmoc); and R$_b$ may be MTr (2,3,6-trimethyl-4-methoxylbenzenesulphonyl). However, the present disclosure is not limited thereto.

In the preparation method of the present disclosure, the reaction between compounds of formulas (I-1) and (I-2), or between compounds of formulas (I-1) and (I-4), or between compounds of formulas (I-5) and (I-6) can be performed with the catalyst of formula (II) or a coupling agent or their combination.

In the conventional method for preparing the cyclopeptide, 3-5 equivalent of coupling agents such as hydroxybenzotriazole (HOBt), 1-hydroxy-7-azabenzotriazole (HOAt), 2-(1H-benzotriazol-1-yl)-1,1,3,3-tetramethyluronium hexafluorophosphate (HBTU) and benzotriazol-1-yl-oxytripyrrolidinophosphonium hexafluorophosphate (PyBOP) are used.

Because these coupling agents are expensive, the obtained cyclopeptide cannot be easily commercialized in large scale and applied to various fields.

In the method for preparing the cyclopeptide of the present disclosure, the catalyst of formula (II) is water soluble and used to facilitate the reaction process. Hence, the expensive coupling agents are not used or combined usage with dramatically reduced amount in the method of the present disclosure. Therefore, cyclopeptide can be produced in a much cheaper manner, and the obtained cyclopeptide can be applied to various fields in practical level of designated purity.

In the method of the present disclosure, when the reactions in the steps (B) to (C) or steps (b) to (d) are performed with the catalyst of formula (II), the catalyst used in the steps (B) to (C) or steps (b) to (d) can be the same or different.

In the catalyst of formula (II), L is a ligand, which preferably is selected from the group consisting of Cl, OTf, OTs, NTf$_2$, halogen, RC(O)CHC(O)R, OAc, OC(O)CF$_3$, OEt, O-iPr, and O-t-butyl, in which R is alkyl (preferably, C$_{1-6}$ alkyl; more preferably, C$_{1-3}$ alkyl). In addition, L$^2$ is also a ligand, which preferably is selected from the group consisting of Cl, H$_2$O, CH$_3$OH, EtOH, THF, CH$_3$CN and Furthermore, in the catalyst of formula (II), M can be a metal preferably selected from the group consisting of IVB, VB, VIB and actinide groups. In one aspect of the present disclosure, M is a group IVB transition element, m is 1 and y is 2; wherein M may be Ti, Zr or Hf. In another aspect of the present disclosure, M is a group VB transition element, m is 1 and y is 2 or 3; wherein M may be V or Nb. In another aspect of the present disclosure, M is a group VIB transition element, m is 1 and y is 4; wherein M may be Mo, W or Cr. In another aspect, M is a group VIB transition element, m is 2 and y is 2; wherein M may be Mo, W or Cr. In further another aspect, M is selected from the actinide group, m is 2 and y is 2; wherein M may be U.

In the present disclosure, specific examples for the catalyst of formula (II) may be MoO$_2$Cl$_2$, V(O)Cl$_2$, V(O)(OAc)$_2$, V(O)(O$_2$CCF$_3$)$_2$, Ti(O)(acac)$_2$, Zr(O)Cl$_2$, Hf(O)Cl$_2$, Nb(O)Cl$_2$, MoO$_2$(acac)$_2$, V(O)(OTs)$_2$, V(O)(NTf$_2$)$_2$, or VO(OTf)$_2$. However, the present disclosure is not limited thereto.

Furthermore, in the catalyst of formula (II), z can be an integer greater than or equal to 0; and preferably, z is 0.

Herein, the cyclopeptide prepared by method of the present disclosure has the structure represented by the following formula (III):

(III)

wherein G' is H or OH;

R$_1$ is in which R$_2$ and R$_3$ are each independently H or C$_{1-6}$ alkyl; X is O, S, CH$_2$, or N—R$_4$, in which R$_4$ is H, C$_{1-6}$ alkyl, (CH$_2$CH$_2$O)$_n$H, —C(=O)—C$_{1-15}$ alkyl, —C(=O)CH$_2$(OC$_2$H$_4$)$_n$OR' or C(=O)(C$_2$H$_4$)$_2$C(=O)O(C$_2$H$_4$O)$_n$R', in which n=1-3 and R' is H or CH$_3$; and

Q is halogen, OC(O)CF$_3$ or OC(O)CH$_3$.

In the cyclopeptide of, X preferably is O, CH$_2$, S or N—R$_4$, wherein R$_4$ is H, C$_{1-6}$ alkyl, —C(=O)—C$_{7-15}$ alkyl, (CH$_2$CH$_2$O)$_n$H, —C(O)CH$_2$(OC$_2$H$_4$)OCH$_3$ or C(=O)(C$_2$H$_4$)$_2$C(=O)O(C$_2$H$_4$O)$_n$H, in which n=1-3.

In the cyclopeptide represented by the formula (III) according to the present disclosure, $R_1$ preferably is wherein $R_2$ is H or $C_{1-6}$ alkyl, $R_3$ is H or $C_{1-6}$ alkyl; and $R_4$ is H, —C(=O)—$C_{7-15}$ alkyl, —C(O)CH$_2$(OC$_2$H$_4$)OCH$_3$ or (CH$_2$CH$_2$O)$_n$H. More preferably, when $R_1$ is $R_2$ is H and $R_3$ is H; or, when $R_1$ is

$R_2$ is isopropyl and $R_3$ is methyl; or, when $R_1$ is

$R_4$ is H or —C(=O)-heptyl.

In the cyclopeptide represented by the formula (III) according to the present disclosure, G' preferably is H; Q preferably is Cl, OC(O)CF$_3$ or OC(O)CH$_3$.

In a preferred aspect of the present disclosure, the cyclopeptide is represented by any one of the following formulas (III-1) to (III-5):

(III-1)

(III-2)

(III-3)

(III-4)

(III-5)

wherein $R_5$ is $C_{1-15}$ alkyl; and Q is Cl, $OC(O)CF_3$ or $OC(O)CH_3$.

The cyclopeptide of the present disclosure comprises amino acids of arginine (R), glycine (G) and aspartate (D), which can bind to the intergrin RGD binding site. When the cyclopeptide of the present disclosure binds to the intergrin RGD binding site of the skin, the communication process between dermis and epidermis can be revived, and the production of important proteins of the basement membrane can be stimulated. Therefore, the purpose of ameliorating scars, wounds, inflammatory processes, aging and/or wrinkle formation can be achieved. Hence, the cyclopeptide of the present disclosure can be applied to topical or cosmetic skin care composition.

In the present disclosure, alkyl, cycloalkyl, aryl, and heteroaryl present in the compounds include both substituted and unsubstituted moieties, unless specified otherwise. Possible substituents on alkyl, cycloalkyl, aryl, and heteroaryl include, but are not limited to alkyl, alkenyl, halogen, alkoxy, ketone, alcohol, thioether, carbamate, amino, heterocyclic group or aryl; but alkyl cannot be substituted with alkyl.

In the present disclosure, the term "halogen" includes F, Cl, Br and I; and preferably is Cl or Br. The term "alkyl" refers to linear and branched alkyl; preferably, includes linear and branched $C_{1-20}$ alkyl; more preferably, includes linear and branched $C_{1-12}$ alkyl; and most preferably, includes linear and branched $C_{1-6}$ alkyl. Specific examples of alkyl include, but are not limited to methyl, ethyl, n-propyl, iso-propyl, n-butyl, sec-butyl, iso-butyl, tert-butyl, pentyl, neo-pentyl or hexyl. The term "alkoxy" refers to a moiety that the alkyl defined in the present disclosure coupled with an oxygen atom; preferably, includes linear and branched $C_{1-20}$ alkoxy; more preferably, includes linear and branched $C_{1-12}$ alkoxy; and most preferably, includes linear and branched $C_{1-6}$ alkoxy. Specific examples of alkoxy include, but are not limited to methoxy, ethoxy, n-propoxy, iso-propoxy, n-butoxy, iso-butoxy, sec-butoxy, tert-butoxy, pentyloxy, neo-pentyloxy or hexyloxy. The term "alkenyl" refers to a linear or branched hydrocarbon moiety that contains at least one double bond; preferably, includes a linear and branched hydrocarbon $C_{2-20}$ moiety containing at least one double bond; more preferably, includes a linear and branched hydrocarbon $C_{2-12}$ moiety containing at least one double bond; and most preferably, includes a linear and branched hydrocarbon $C_{2-6}$ moiety containing at least one double bond. Specific examples of alkenyl include, but are not limited to ethenyl, propenyl, allyl, or 1,4-butadienyl. The term "aryl" refers to a monovalent 6-carbon monocyclic, 10-carbon bicyclic, or 14-carbon tricyclic aromatic ring system. Specific examples of aryl include, but are not limited to phenyl, naphthyl, pyrenyl, anthracenyl or phenanthryl; and preferably, the aryl is phenyl. The term "heterocyclic group" refers to a 5-8 membered monocyclic, 8-12 membered bicyclic or 11-14 membered tricyclic heteroaryl or heterocycloalkyl having at least one heteroatom which is selected from the group consisting of O, S and N. Specific examples of heterocyclic group include, but are not limited to pyridyl, pyrimidinyl, furyl, thiazolyl, imidazolyl or thienyl.

Other objects, advantages, and novel features of the present disclosure will become more apparent from the following detailed description when taken in conjunction with the accompanying drawings.

DETAILED DESCRIPTION OF THE PREFERRED EMBODIMENT

The present disclosure has been described in an illustrative manner, and it is to be understood that the terminology used is intended to be in the nature of description rather than of limitation. Many modifications and variations of the present disclosure are possible in light of the above teachings. Therefore, it is to be understood that within the scope of the appended claims, the invention may be practiced otherwise than as specifically described.

The cyclopeptide of one preferred embodiment of the present disclosure can be prepared as follows.

[Scheme I-1]

-continued

-continued

To a solution of Fmoc-Gly-OH (5.866 g, 20 mmol, 1.0 equiv) in CH$_3$CN (200 mL) was added catalyst ZrOCl$_2$ (5 mol %), N-ethyl-N'-(3-dimethylaminopropyl)-carbodiimide HCl (EDCI.HCl) (4.970 g, 26 mmol, 1.3 equiv) and N-Hydroxysuccinimide (NHS) (2.53 g, 22 mmol, 1.1 equiv) at room temperature under N$_2$ atmosphere and the reaction was monitored by TLC analysis. The reaction was stirred at room temperature for 4 h till the starting Fmoc-Gly-OH was totally consumed and cooled to 0° C. A solution of H-Asp(O$^t$Bu)-OH (3.98 g, 21 mmol, 1.05 equiv) and NaHCO$_3$ (1.77 g, 21 mmol, 1.05 equiv) in 100 mL H$_2$O was added to the above solution via syringe at room temperature. The reaction mixture was stirred at room temperature for 16 h. Solvent was evaporated, and the remaining residue was acidified to pH 3.2-3.4 with diluted aqueous HCl (0.1 N) and the white solid was precipitated out from the aqueous solution. The white solid was filtered and washed with H$_2$O and the crude product was recrystallized in 60% aqueous ethanol to afford Fmoc-Gly-Asp(O$^t$Bu)-OH as a white solid (8.521 g, 91% yield). $^1$H NMR (500 MHz, CDCl$_3$): δ 7.74 (d, 2H, J=7.6 Hz), 7.56 (d, 2H, J=5.0 Hz), 7.36 (d, 3H, J=7.5 Hz), 7.28 (d, 2H, J=7.4 Hz), 5.83 (s, 1H), 4.83 (q, 1H, J=4.5 Hz), 4.34 (q, 2H, J=6.5 Hz), 4.18 (t, 2H, J=6.5 Hz), 4.02 (d, 1H, J=16 Hz), 3.88 (d, 1H, J=16.6 Hz), 2.94 (dd, 1H, J=16.7, 3.1 Hz), 2.76 (dd, 1H, J=16.8, 4.2 Hz), 1.38 (s, 9H); HRMS (ESI), calculated for C$_{25}$H$_{28}$N$_2$NaO$_7$ ([M+Na]+): 491.1794, found: 491.1797.

[Scheme I-2]

+

A dry microwave vial was added Fmoc-Pip(Boc)-OH (2.33 g, 5 mmol, 1.0 equiv), H-Arg(Mtr)-OMe (2.2 g, 5.5 mmol, 1.0 equiv), catalyst ZrOCl$_2$ (5 mol %), and N,N,N',N'-tetramethylchloroformamidinium hexafluorophosphate (TCFH) (1.995 g, 6 mmol, 1.20 equiv) in dry CH$_3$CN (2 mL/mmol) under argon. Subsequently, 1-Methyl imidazole (NMI) (0.837 mL, 10.5 nmol, 2.1 equiv) was added and the vial was sealed and heated in an oil bath at 70° C. for 12 h (CAUTION: Heating CH$_3$CN causes pressure increase in the reactor). The reaction mixture was cooled to room temperature and diluted with water, saturated aqueous NaHCO$_3$ and extracted with ethyl acetate. The collected organic phases were combined and washed with brine, dried over Na$_2$SO$_4$ and concentrated.

The crude product was purified by flash column chromatography under the conditions indicated give Fmoc-Pip(Boc)-Arg(Mtr)-OMe as a light yellow solid (3.648 g, 86% yield). $^1$H NMR (500 MHz, CDCl$_3$): δ 7.73 (d, 2H, J=7.5 Hz), 7.51 (t, 2H, J=3.0 Hz), 7.37 (t, 3H, J=7.0 Hz), 7.26-7.05 (m, 10H), 7.05 (br, 1H), 6.52 (s, 1H), 5.94 (br, 1H), 4.44-4.39 (m, 2H), 4.31 (q, 1H, J=5.2 Hz), 4.13 (t, 1H, J=6.5 Hz), 3.77 (s, 3H), 3.82-3.77 (m, 2H), 3.59 (s, 3H), 3.59 (m, 2H), 3.27-3.10 (m, 3H), 3.08-2.76 (m, 1H), 2.78-2.61 (m, 1H), 3.77 (s, 3 h), 2.56 (s, 3H), 2.00-1.84 (m, 4H), 1.82 (t, 1H, J=6.3 Hz), 1.77-1.54 (m, 2H), 1.40 (s, 9H); HRMS (ESI), calculated for C$_{43}$H$_{56}$N$_6$NaO$_{10}$S ([M+Na]+): 871.3676, found: 871.3672.

[Scheme I-3]

To a MeOH solution (100 mL) of Fmoc-Pip(Boc)-Arg(Mtr)-OMe (2.24 g, 2.64 mmol, 1.0 equiv) was added 20 equivalents of piperidine. The reaction mixture was then stirred until complete consumption of the Fmoc-Pip(Boc)-Arg(Mtr)-OMe as confirmed by TLC (1 h) and the reaction mixture was then evaporated to dryness under reduced pressure at room temperature. A piperidine adduct of dibenzofulvene was washed out with hexane and the resulting H-Pip(Boc)-Arg(Mtr)-OMe was dried in vacuo and used directly for the next step. To a dry microwave vial was added Fmoc-D-Phe-OH (1.123 g, 2.9 mmol, 1.1 equiv), H-Pip(Boc)-Arg(Mtr)-OMe (1.0 equiv), catalyst $ZrOCl_2$ (5 mol %), and TCFH (1.02 g, 3.17 mmol, 1.2 equiv) in dry $CH_3CN$ (2 mL/mmol) under argon. Subsequently, 1-Methyl imidazole (NMI) (0.443 mL, 5.55 mmol, 2.1 equiv) was added and the vial was sealed and then heated in an oil bath at 70° C. for 12 h (CAUTION: Heating $CH_3CN$ causes pressure increase in the reactor). The reaction mixture was cooled to room temperature and diluted with water, saturated aqueous $NaHCO_3$ and extracted with ethyl acetate. The collected organic phases were combined and washed with brine, dried over $Na_2SO_4$ and concentrated. The crude product was purified by flash column chromatography under the conditions indicated give Fmoc-Phe-Pip(Boc)-Arg(Mtr)-OMe as a light yellow solid (1.865 g, 71% yield relative to the amount of Fmoc-Pip(Boc)-Arg(Mtr)-OMe). $^1H$ NMR (500 MHz, $CDCl_3$): δ 7.75 (d, 2H, J=7.0 Hz), 7.56 (t, 2H, J=7.5 Hz), 7.39 (t, 3H, J=7.4 Hz), 7.30-7.17 (m, 10H), 6.51 (s, 1H), 6.05 (br, 1H), 4.46-4.42 (m, 2H), 4.42-4.23 (m, 2H), 4.20 (t, 1H, J=6.7 Hz), 3.88-3.78 (m, 2H), 3.80 (s, 3H), 3.66 (s, 3H), 3.38-3.34 (m, 1H), 3.19-2.97 (m, 3H), 32.92-2.76 (m, 2H), 2.75-2.61 (m, 2H), 2.67 (s, 3H), 2.57 (s, 3H), 2.11 (s, 3H), 1.96-1.77 (m, 4H), 1.76-1.67 (m, 1H), 1.67-1.54 (m, 1H), 1.42 (t, 1H, J=6.3 Hz), 1.37 (s, 9H); HRMS (ESI), calculated for $C_{52}H_{65}N_7NaO_{11}S$ ([M+Na]+): 1018.4361, found: 1018.4356.

[Scheme I-4]

-continued

To a stirred MeOH solution (10 mL) of Fmoc-D-Phe-Pip(Boc)-Arg(Mtr)-OMe (996 mg, 1.0 mmol, 1.0 equiv) was added 20 equivalents of piperidine, and the reaction mixture was stirred until complete consumption of the Fmoc-D-Phe-Pip(Boc)-Arg(Mtr)-OMe as confirmed by TLC (1 h) and the reaction mixture was then evaporated to dryness under a reduced pressure at room temperature. A piperidine adduct of dibenzofulvene was washed out with hexane and the resulting H-D-Phe-Pip(Boc)-Arg(Mtr)-OMe was dried in vacuo and used directly for the next step. To a dry vial was added Fmoc-Gly-Asp(O$^t$Bu)-OH (535 mg, 1.1 mmol, 1.1 equiv), H-D-Phe-Pip(Boc)-Arg(Mtr)-OMe (1.0 equiv), catalyst ZrOCl$_2$ (5 mol %), and 1-hydroxy-7-azabenzotriazole (HOAt) (1.2 equiv) in dry CH$_3$CN (2 mL/mmol) under argon and stirred at room temperature for 10 minutes. EDCI.HCl (229 mg, 1.2 mmol, 1.2 equiv) was then added in four portions followed by the addition of N-methylmorpholine (NMM) (167 μL, 2.1 mmol, 2.1 equiv) and the reaction mixture was stirred at room temperature for 12 hours. The reaction was diluted with ethyl acetate and washed with diluted HCl (0.1 N), water, saturated aqueous NaHCO$_3$ and extracted with ethyl acetate. The collected organic phase was dried over Na$_2$SO$_4$ and concentrated. The crude product was purified by flash column chromatography under the conditions indicated give Fmoc-Gly-Asp(O$^t$Bu)-D-Phe-Pip(Boc)-Arg(Mtr)-OMe as a light yellow solid (1.016 g, 83% yield relative to the amount of Fmoc-D-Phe-Pip(Boc)-Arg(Mtr)-OMe). $^1$H NMR (500 MHz, CDCl$_3$): δ 7.74 (d, 2H, J=7.0 Hz), 7.55 (t, 2H, J=7.5 Hz), 7.37 (t, 3H, J=7.5 Hz), 7.30-7.17 (m, 10H), 6.52 (s, 1H), 6.05 (br, 1H), 4.61-4.41 (m, 2H), 4.41-4.21 (m, 2H), 4.21 (t, 1H, J=6.7 Hz), 3.91-3.72 (m, 2H), 3.82 (s, 3H), 3.67 (s, 3H), 3.39-3.32 (m, 1H), 3.33-3.21 (m, 2H), 3.18-2.98 (m, 3H), 2.73-2.86 (m, 2H), 2.82-2.67 (m, 2H), 2.66 (s, 3H), 2.56 (s, 3H), 2.25-2.03 (m, 2H), 2.11 (s, 3H), 1.84-1.82 (m, 4H), 1.74-1.61 (m, 3H), 1.42 (s, 9H), 1.37 (s, 9H); HRMS (ESI), calculated for C$_{62}$H$_{81}$N$_9$NaO$_{15}$S ([M+Na]+): 1246.5471, found: 1246.5477.

[Scheme I-5]

Fmoc-Gly-Asp(O$^t$Bu)-D-Phe-Pip(Boc)-Arg(Mtr)-OMe (568 mg, 0.462 mmol, 1.0 equiv) was dissolved in 20 ml of methanol, lithium hydroxide (12 mg, 0.485 mmol, 1.05 equiv) was added and the mixture was stirred for 2.5 hours at 25° C. After evaporation, the residue was dissolved in water, acidified to pH=3 with dilute HCl (0.1 N) and extracted with ethyl acetate. The extract was dried over Na$_2$SO$_4$, evaporated again and the obtained Fmoc-Gly-Asp(O$^t$Bu)-D-Phe-Pip(Boc)-Arg(Mtr)-OH was stirred at 25° C. for 1 hour with piperidine (15 equiv) in MeOH (10 mL). The mixture was evaporated and the piperidine adduct of dibenzofulvene was washed out with diethyl ether. The obtained H-Gly-Asp(O$^t$Bu)-D-Phe-Pip(Boc)-Arg(Mtr)-OH was dissolved in a mixture of dichloromethane (2 mL) and CH$_3$CN (8 mL), and cooled to 0° C. To this solution was added catalyst ZrOCl$_2$ (5 mol %), 1-hydroxy-7-azabenzotriazole (HOAt) (1.1 eq) and N-ethyl-N'-(3-dimethylaminopropyl)-carbodiimide.HCl (EDC.HCl) (102 mg, 0.531 mmol, 1.15 eq) at 0° C. under N$_2$ atmosphere and stirred at 0° C. for 20 minutes. N-Methylmorpholine (107 µL, 0.97 mmol, 2.0 eq) was slowly added via syringe at 0° C., the temperature of the reaction was gradually warmed to room temperature, and then it was stirred at room temperature for 16 hours. Solvent was evaporated, and the remaining residue was suspended in EtOAc (25 mL), and the pH value was adjusted to 3.5-4.0 with 0.1 N HCl. The organic layer was separated and washed with H$_2$O (10 mL), saturated aqueous NaHCO$_3$ (10 mL), brine (10 mL), and dried over Na$_2$SO$_4$. After the evaporation of solvent, the remaining residue was purified by silica gel flash chromatography under the conditions indicated to provide cyclo-Gly-Asp(O$^t$Bu)-D-Phe-Pip(Boc)-Arg(Mtr) (184 mg, 41% yield relative to the amount of Fmoc-Gly-Asp(O$^t$Bu)-D-Phe-Pip(Boc)-Arg(Mtr)-OMe). $^1$H NMR (500 MHz, CDCl$_3$): δ 7.70 (br, 1H), 7.40-7.38 (m, 5H), 6.56 (s, 1H), 6.05 (br, 1H), 4.46-4.23 (m, 2H), 3.94-3.77 (m, 2H), 3.84 (s, 3H), 3.28-3.21 (m, 1H), 3.20-3.08 (m, 3H), 2.92-2.71 (m, 4H), 2.21-2.08 (m, 3H), 2.12 (s, 3H), 1.88-1.83 (m, 3H), 1.72-1.69 (m, 2H), 1.62-1.60 (m, 1H), 1.52-1.47 (m, 1H), 1.44 (s, 9H), 1.38 (s, 9H), 1.29-1.25 (m, 2H); HRMS (ESI), calculated for C$_{46}$H$_{67}$N$_9$NaO$_2$S ([M+Na]+): 992.4527, found: 992.4521.

[Scheme I-6]

The protected cyclopeptide cyclo-Gly-Asp(O'Bu)-D-Phe-Pip(Boc)-Arg(Mtr) (120 mg, 0.124 mmol) was treated with 2 mL of a solution of TFA (80%), phenol (5%), water (2.5%), thioanisole (5%), triisopropylsilane (2.5%) and 1,2-ethanedithiol (5%) at ambient temperature. After 9 hours, the solvent was evaporated in vacuo. The residue was dissolved in 0.1 N HCl and freeze-dried after each dissolving operation six times. The resulting solid was precipitated with cold diethyl ether (5 mL×2) and centrifuged. The resulting pellet was washed several times with cold diethyl ether to provide cyclo-Gly-Asp-D-Phe-Pip-Arg.2HCL as pale yellow solid (78 mg, 94%, relative to the amount of cyclo-Gly-Asp(O'Bu)-D-Phe-Pip(Boc)-Arg(Mtr). $^1$H NMR (500 MHz, D$_2$O): δ 7.26-7.08 (m, 5H), 4.51 (t, 1H, J=6.7 Hz), 4.47-4.23 (m, 2H), 4.41-4.37 (m, 1H), 3.84-3.79 (m, 1H), 3.78-3.76 (m, 1H), 3.70-3.67 (m, 1H), 3.54-3.50 (m, 1H), 3.19-3.17 (m, 311), 3.06-3.02 (m, 4H), 3.02-2.97 (m, 3H), 2.75-2.72 (m, 2H), 2.66-2.63 (q, 2H, J=7.9 Hz), 2.46-2.39 (m, 4H), 2.14-2.10 (m, 2H), 2.09-2.01 (m, 4H), 1.82-1.77 (m, 2H), 1.68-1.61 (m, 2H), 1.50-1.46 (m, 2H), 1.44-1.40 (m, 2H), 1.29-1.25 (m, 2H); HRMS (ESI), calculated for C$_{27}$H$_{43}$Cl$_2$N$_9$NaO$_7$ ([M+Na+2H+]): 698.25602, found: 698.2572.

The cyclopeptide of a preferred embodiment of the present disclosure can be prepared by the following method.

[Scheme II-1]

-continued

C5P-3

To a stirred CH$_2$Cl$_2$ or THF solution (3.5 mL) of C5P-1 (740 mg, 0.76 mmol, 1.0 equiv) was added 10-15 equivalents of piperidine (8.4 mmol), and the reaction mixture was stirred until complete consumption of the C5P-1 confirmed by TLC (0.5-1 hour). The reaction mixture was then evaporated to dryness with toluene under reduced pressure at 60° C.

A piperidine adduct of dibenzofulvene was washed out with hexane and the resulting C5P-2 (LC-MS: t$_R$ 5.2 minutes for 91% purity) was dried in vacuo and used directly for the next step. To a dry microwave vial was added C5P-2 (900 mg, 1.2 mmol, 1.0 equiv), Fmoc-Asp(O$^t$Bu)-OH (986 mg, 2.4 mmol, 2.0 equiv), catalyst ZrOCl$_2$ (5 mol %), N-(3-dimethylaminopropyl)-N'-ethylcarbodiimide hydrochloride (EDCI) (344 mg, 1.8 mmol, 1.5 equiv), and hydroxybenzotriazole (HOBt) (278 mg, 1.8 mmol, 1.5 equiv) in dry CH$_3$CN (6 mL) under argon. N,N-Diisopropylethylamine (DIPEA) (232 mg, 1.8 mmol, 1.5 equiv) was subsequently added and the vial was sealed at 20-25° C. for 0.5 hour. The reaction mixture was diluted with water, saturated aqueous NaHCO$_3$ and extracted with ethyl acetate. The collected organic phases were combined and washed with brine, dried over Na$_2$SO$_4$ and concentrated. The crude product was purified by flash column chromatography under the conditions indicated to give C5P-3 as a light yellow solid (1.370 g, 72.2% conversion yield; LC-MS: t$_R$ 7.15 minutes).

[Scheme II-2]

-continued

C5P-5

In a solution of EtOAc/MeOH (25/25 mL) was placed C5P-3 (685 mg, 0.6 mmol, 1 equiv) and Pd/C (10% wt, 70 mg). Hydrogenolysis was carried out at ambient temperature for 18 hours. The reaction mixture was filtered and concentrated to give crude C5P-4 (645 mg, 71.6% conversion yield; LC-MS: $t_R$ 5.50 minutes). The crude acid C5P-4 (645 mg, 0.61 mmol, 1.0 equiv) obtained after debenzylation was treated with glycine methyl ester hydrochloride (152 mg, 1.22 mmol, 2 equiv), catalyst $ZrOCl_2$ (5 mol %), EDCI (174 mg, 0.91 mmol, 1.5 equiv), and $HOBt-H_2O$ (142 mg, 0.91 mmol, 1.5 equiv) in dry $CH_3CN$ (6 mL) under argon. DIPEA (275 mg, 2.13 mmol, 3.5 equiv) was subsequently added and the reaction was stirred at 20-25° C. for 2.5 hours. The reaction mixture was diluted with water (4 mL), saturated aqueous $NaHCO_3$ (4 mL) and extracted with ethyl acetate. The collected organic phases were combined and washed with brine, dried over $Na_2SO_4$ and concentrated.

The crude product was purified by flash column chromatography under the conditions indicated to give C5P-5 as a light yellow oil (417 mg, 97.53% conversion yield; LC-MS: $t_R$ 6.56 min).

[Scheme II-3]

C5P-5

1. 20% piperidine Dichloromethane
2. cat $ZrOCl_2$ 10 mol % $La(OTf)_3$ CPME

C5P-7

CP5-5 (834 mg, 0.76 mmol, 1.0 equiv) was dissolved in $CH_2Cl_2$ or THF solution (3.5 mL), the solution was stirred, followed by adding 10-15 equivalents of piperidine (8.14 mmol). The reaction mixture was stirred until complete consumption of the C5P-5 confirmed by TLC (0.5-1 h) and the reaction mixture was then evaporated to dryness under a reduced pressure at ambient temperature. A piperidine adduct of dibenzofulvene was washed out with hexane and the resulting C5P-6 (LC-MS: $t_R$ 5.06 min for 92.84% purity) was dried in vacuum and used directly for the next step. To a dry reaction sealed vial was added C5P-6 (200 mg, 0.22 mmol, 1.0 equiv), catalyst $V(O)Cl_2$, $Ti(O)(acac)_2$ or $ZrOCl_2$ (5-10 mol %) in dry $CH_3CN$, cyclopentyl methyl ether (CPME), or toluene (1.6-2.2 mL). Subsequently, 1,8-diazabicyclo(5.4.0)undec-7-ene (DBU) (10 mg, 0.066 mmol, 0.3 equiv) was added and the vial was sealed at 80-110° C. for 7-23.5 hours. The reaction mixture was concentrated and then diluted with water, saturated aqueous $NaHCO_3$ and extracted with ethyl acetate. The collected organic phases were combined and washed with brine, dried over $Na_2SO_4$ and concentrated. The crude product was purified by flash column chromatography under the conditions indicated to give C5P-7 as a light yellow solid (0.1370 g, 71.55% conversion yield; LC-MS: $t_R$ 4.98 min).

[Scheme II-4]

C5P-7

TFA →

C5P-7 (300 mg, 0.34 mmol, 1 equiv) was dissolved in TFA (15 mL) and stirred at ambient temperature for 18-19 hours. The reaction mixture was concentrated to give crude C5P (~200 mg, 94.4% conversion yield; LC-MS: $t_R$ 2.03 min). The crude C5P was washed with IPA/IPE (2/1) to get pure C5P and stored as a TFA salt with addition of 1 equiv of TFA.

Anti-aging Evaluation Type I collagen is the primary component of the skin dermis. Both the quantity and quality of extracellular collagen are primarily related to skin ageing. The present embodiment was examined, by using Procollagen Type I C-Peptide (PIP) EIA Kit, effects of induction of procollagen secretion and cytotoxicity in respect of hs68 human fibroblasts. The results are shown in the following Table 1.

TABLE 1

| TGFβ Conc. (μM) | 0.83 | — | — | — | — | — | — | — |
|---|---|---|---|---|---|---|---|---|
| Cyclopeptide Conc.[a] (μM) | — | 0.0008 | 0.004 | 0.02 | 0.1 | 0.25 | 0.5 | — |
| Procollagen Type I (ng/mL) | 320 | 235 | 225 | 220 | 208 | 208 | 184 | 90 |
| Cell viability[b] (%) | 95 | 92 | 97 | 100 | 97 | 99 | 100 | 100 |

[a](III-5) was under test, in which Q is Cl.
[b]cell viability (%) = (sample/control) × 100%

It can be found in the experimental results that each of the tested cyclopeptides in different concentrations can promote the secretion of procollagen type I. When the cyclopeptide concentration is as low as 0.0008 μM, it can increase the secretion amount of procollagen type I by 2.5 times. It is therefore predicted that the cyclopeptide can repair skin aging. In addition, all the cell viabilities are greater than 80%, indicating that the cyclopeptide has no cytotoxicity.

MMP-1 Inhibition Test

Matrix Metalloproteinase-1 (MMP-1) is one of collagenases, and is involved in the degradation of the extracellular matrix (ECM). In details, fibroblasts result in the overexpression of MMP-1 after exposure to UV-containing sunlight, so that the ECM is then degraded by MMP-1.

To examine the effect of the cyclopeptide of the present disclosure, a series of MMP-1 inhibition test was conducted.

Matrix metalloproteinases (MMPs) are involved in skin physiological functions such as wound healing, aging, and inflammatory responses. The MMPs plays an important role in maintaining normal physiological functions or pathological phenomena of skin. In addition, skin aging results in various impacts on the skin, including wrinkles, dryness, anetoderma, inhibition of collagen production, and promotion of MMP, which accelerates the degradation of the extracellular matrix (ECM). As a result, skin elasticity and skin water-holding capacity are lost.

In this test, test compound and human fibroblasts were co-cultured, and cytokine tumor necrosis factor-α (TNF-α) was added as an inducer to induce the expression of MMP-1 to a high level. Then, the test compound was evaluated for the ability of reducing the MMP-1 level induced by TNF-α.

Material and Method

Test compound: cyclopeptide (III-3) of the present disclosure, in which Q is Cl.
Cell line: skin fibroblast Hs68

First, the seeding of skin fibroblast Hs68 cells onto culture medium dish was conducted overnight, and then different concentrations (0.05 μM, 0.25 μM, 1.25 μM, 2.5 μM and 5 μM) of cyclopeptide (III-3) were added to the skin fibroblast cells for 6 hours, which was further incubated with TNF-α (20 ng/mL) for 42 hours. Afterwards, the concentrations of MMP-1 in each group were measured by ELISA, and the results are shown in Table 2.

TABLE 2

| | Control[c] | TNF-α | Test 1 | Test 2 | Test 3 | Test 4 | Test 5 | Positive control[d] |
|---|---|---|---|---|---|---|---|---|
| TNF-α Conc. (ng/mL) | — | 20 | 20 | 20 | 20 | 20 | 20 | 20 |
| Cyclopeptide Conc. (μM) | — | — | 0.05 | 0.25 | 1.25 | 2.5 | 5 | — |
| RA Conc. (μM) | — | — | — | — | — | — | — | 3.3 |
| MMP-1 Conc. (pg/mL) | 243.8 | 604.4 | 337.8 | 244.2 | 212.7 | 194.2 | 168.6 | 155.9 |

[c]control group is the group without adding TNF-α, cyclopeptide and retinoic acid (RA).
[d]RA is a known MMP-1 inhibitor, and the positive control is the group added with RA.

According to the results above, compared to 3.3 μM of RA (set as 100%), 0.05 μM of cyclic peptide (III-3) could inhibit MMP-1 by about 60%, and 0.25 μM of cyclopeptide (III-3) could inhibit about 80% of MMP-1; 1.25 μM of cyclopeptide (III-3) could almost inhibit 87% of MMP-1; 2.5 μM cyclopeptide (III-3) could almost inhibit 91% of MMP-1.

Figure 1:
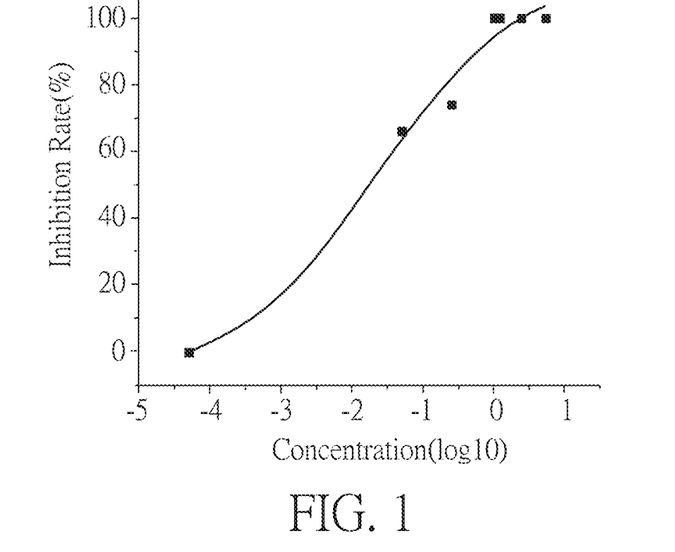
FIG. 1 is a graph showing the relationship between the inhibition rate and concentration of cyclopeptide (III-3).

In addition, the result shown in FIG. 1 was obtained by measuring the inhibition concentration of cyclopeptide (III-3), thereby calculating the $IC_{50}$ of cyclopeptide (III-3), which was 0.02 μM.

Likewise, the aforementioned MMP-1 inhibition test was conducted with different concentrations (0.05 μM, 0.25 μM, 1.25 μM, 2.5 μM and 5 μM) of the cyclopeptide (III-1) (Q is Cl), and the results were shown in the following Table 3. It could be found from Table 3 that 0.05 μM of cyclopeptide (III-1) could inhibit 12% of MMP-1, 0.25 μM of cyclopeptide (III-1) could inhibit 38% of MMP-1, and 1.25 μM of cyclopeptide (III-1) could inhibit 90% of MMP-1.

TABLE 3

| | Control[c] | TNF-α | Test 6 | Test 7 | Test 8 | Test 9 | Positive control[d] |
|---|---|---|---|---|---|---|---|
| TNF-α Conc. (ng/mL) | — | 20 | 20 | 20 | 20 | 20 | 20 |

TABLE 3-continued

| | Control[c] | TNF-α | Test 6 | Test 7 | Test 8 | Test 9 | Positive control[d] |
|---|---|---|---|---|---|---|---|
| Cyclopeptide Conc. (μM) | — | — | 0.05 | 0.25 | 1.25 | 2.5 | — |
| RA Conc. (μM) | — | — | — | — | — | — | 3.3 |
| MMP-1 Conc. (pg/mL) | 304.2 | 442.2 | 422.3 | 378.2 | 288.0 | 271.8 | 271.3 |

[c]control group is the group without adding TNF-α, cyclopeptide and retinoic acid (RA).
[d]RA is a known MMP-1 inhibitor, and the positive control is the group added with RA.

Figure 2:
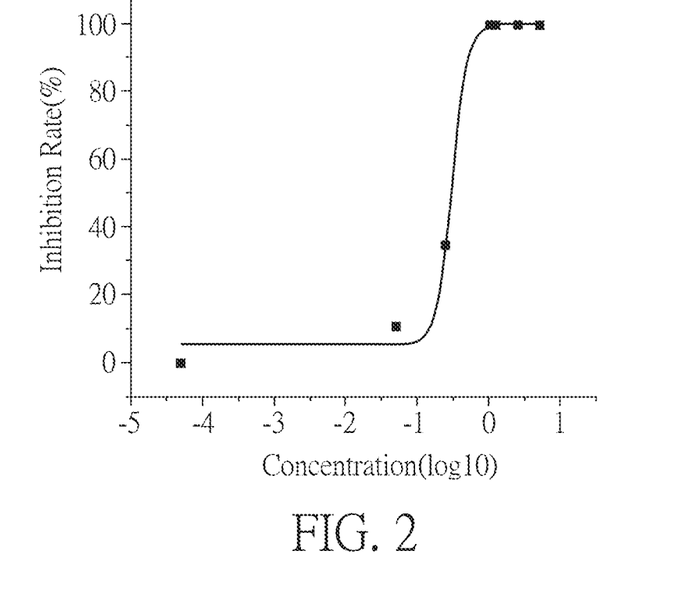
FIG. 2 is a graph showing the relationship between the inhibition rate and concentration of cyclopeptide (III-1).

In addition, the result shown in FIG. 2 was obtained by measuring the inhibition concentration of cyclopeptide (III-1), thereby calculating the $IC_{50}$ of cyclopeptide (III-1), which is 0.7 μM.

Although the present disclosure has been explained in relation to its preferred embodiment, it is to be understood that many other possible modifications and variations can be made without departing from the spirit and scope of the disclosure as hereinafter claimed.

What is claimed is:

1. A method for preparing a cyclopeptide, comprising the following steps:

(A) providing compounds represented by the following formulas (I-1) and (I-2):

wherein, $R_a$, $R_b$ and $R_e$ are each independently a protection group;
$R_c$ and $R_d$ are each independently alkyl, cycloalkyl, aryl or heteroaryl;
G is H, or O-t-Bu; and
$R_1$ is in which $R_2$ and $R_3$ are each independently H or $C_{1-6}$ alkyl;
X is O, S, $CH_2$, or N—$R_4$, in which $R_4$ is H, $C_{1-6}$ alkyl, $(CH_2CH_2O)_nH$, —C(=O)—$C_{1-15}$ alkyl, —C(=O)$CH_2$ $(OC_2H_4)_n OR'$ or $C(=O)(C_2H_4)_2C(=O)O(C_2H_4)_nR'$, in which n=1-3 and R' is H or $CH_3$;

(B) performing a reaction between the compounds of formulas (I-1) and (I-2) to obtain a compound represented by the following formula (I-3):

and (C) performing a cyclization reaction of the compound of formula (I-3) with a catalyst of formula (II) and deprotection to obtain a compound represented by the following formula (III):

$$M(O)_m L^1_y L^2_z \quad (II)$$

wherein G' is H or OH;
Q is halogen, $OC(O)CF_3$ or $OC(O)CH_3$;
M is a metal selected from the group consisting of IVB, VB, VIB and actinide groups;
$L^1$ and $L^2$ respectively is a ligand;
m and y are integers greater than or equal to 1; and
z is an integer greater than or equal to 0.

2. The method of claim 1, wherein $L^1$ is selected from the group consisting of Cl, OTf, OTs, $NTf_2$, halogen, RC(O) $CH_2C(O)R$, OAc, $OC(O)CF_3$, OEt, O-iPr and O-t-butyl, in which R is alkyl.

3. The method of claim 1, wherein $L^2$ is selected from the group consisting of Cl, $H_2O$, $CH_3OH$, EtOH, THF, $CH_3CN$, and 4. The method of claim 1, wherein $R_a$ and $R_e$ are fluorenylmethyloxycarbonyl, and $R_b$ is 2,3,6-trimethyl-4-methoxylbenzenesulphonyl.

5. The method of claim 1, wherein M is a group IVB transition element, m is 1 and y is 2.

6. The method of claim 1, wherein M is a group VB transition element, m is 1 and y is 2 or 3.

7. The method of claim 1, wherein M is a group VIB transition element, m is 1 and y is 4.

8. The method of claim 1, wherein M is a group VIB transition element, m is 2 and y is 2.

9. The method of claim 1, wherein M is selected from the actinide group, m is 2 and y is 2.

10. The method of claim 1, wherein the catalyst of formula (II) is $MoO_2Cl_2$, $V(O)Cl_2$, $V(O)(OAc)_2$, $V(O)(O_2CCF_3)_2$, $Ti(O)(acac)_2$, $Zr(O)Cl_2$, $Hf(O)Cl_2$, $Nb(O)Cl_2$, $MoO_2(acac)_2$, $V(O)(OTs)_2$, $VO(OTf)_2$, or $V(O)(NTf_2)_2$.

11. The method of claim 1, wherein z is 0.

12. The method of claim 1, wherein the compound of formula (III) is any one of formulas (III-1) to (III-5):

wherein $R_5$ is $C_{1-15}$ alkyl.

* * * * *